(12) United States Patent
Hummel

(10) Patent No.: US 7,262,843 B2
(45) Date of Patent: Aug. 28, 2007

(54) METHOD AND DEVICE FOR CORRECTING FOR THE SIZE AND/OR SHAPE OF A MEASURING VOLUME IN A CHEMICAL AND/OR BIOLOGICAL SAMPLE

(75) Inventor: Stefan Hummel, Haseldorf (DE)

(73) Assignee: Evotec AG, Hamburg (DE)

( * ) Notice: Subject to any disclaimer, the term of this patent is extended or adjusted under 35 U.S.C. 154(b) by 307 days.

(21) Appl. No.: 10/496,589

(22) PCT Filed: Nov. 19, 2002

(86) PCT No.: PCT/EP02/12938

§ 371 (c)(1),
(2), (4) Date: May 24, 2004

(87) PCT Pub. No.: WO03/044495

PCT Pub. Date: May 30, 2003

(65) Prior Publication Data
US 2004/0257590 A1 Dec. 23, 2004

(30) Foreign Application Priority Data
Nov. 23, 2001 (DE) .................... 101 57 511

(51) Int. Cl.
*G01J 3/30* (2006.01)
(52) U.S. Cl. .................................... 356/317
(58) Field of Classification Search ............. 356/317, 356/318, 382
See application file for complete search history.

(56) References Cited

U.S. PATENT DOCUMENTS

| | | | |
|---|---|---|---|
| 5,319,498 A * | 6/1994 | Hara et al. .......... 359/824 |
| 5,834,758 A | 11/1998 | Trulson et al. | |
| 5,981,956 A | 11/1999 | Stern | |
| 6,038,404 A * | 3/2000 | Suzuki et al. ............ 396/79 |
| 6,130,745 A * | 10/2000 | Manian et al. .......... 356/123 |
| 6,548,796 B1 * | 4/2003 | Silvermintz et al. ..... 250/201.3 |
| 2005/0036667 A1 * | 2/2005 | So et al. .................. 382/128 |

FOREIGN PATENT DOCUMENTS

| WO | WO99/47963 | 9/1999 |
|---|---|---|
| WO | WO 00/46590 | 8/2000 |

OTHER PUBLICATIONS

German Search Report, dated May 24, 2002.
Nachr. Chem. Tech. Lab., 38, Nr. 10, 1990, Seiten M 2-M 23.
Volcker, Martin et al, "Mikroskopgestutzte Fluoreszenz-Photonen-Korrelation", tm-Technisches Messen, 63, 1996, Seite 128-135.
International Search Report, completed Jun. 3, 2003.

* cited by examiner

Primary Examiner—Layla G. Lauchman
Assistant Examiner—Jarreas Underwood
(74) Attorney, Agent, or Firm—Griffin & Szipl, P.C.

(57) ABSTRACT

In a method for correcting for the size and/or shape of a measuring volume (18)in a chemical and/or biological sample (14), especially in fluorescence spectroscopy, a measuring volume (18) located within the sample (14) is imaged to a detector means (44), using observing optics (32). The imaging is effected through a sample carrier wall (16) of a sample carrier (12) containing the sample (14). In the next step, the thickness of the sample carrier wall (16) is automatically determined. Thereafter, at least one lens (28) is shifted automatically along an optical axis of the observing optics (32) to correct for the size and/or shape of the measuring volume (18) as a function of the thickness of the sample carrier wall (16).

25 Claims, 3 Drawing Sheets

US 7,262,843 B2

METHOD AND DEVICE FOR CORRECTING FOR THE SIZE AND/OR SHAPE OF A MEASURING VOLUME IN A CHEMICAL AND/OR BIOLOGICAL SAMPLE

This is a National Phase Application in the United States of International Patent Application No. PCT/EP2002/012938 filed Nov. 19, 2002, which claims priority on German Patent Application No. 10157511.4, filed Nov. 23, 2001. The entire disclosures of the above patent applications are hereby incorporated by reference.

1. Field of the Invention

The invention refers to a method for correcting for the size and/or the shape of a measuring volume in a chemical and/or biological sample, especially in fluorescence spectroscopy. The invention further refers to a device for executing the method.

2. Background of the Invention

The examination of samples is often performed using microscopes or similar suitable optical devices. Here, the samples are arranged on slides or other suitable sample carriers, such as titer plates, for example. Often observing or examining a sample is performed through a transparent bottom of a sample carrier. Observing through a bottom of a sample carrier is advantageous, for example, in that the observation objective may be arranged below the sample carrier, while, for example, pipetting means for feeding the samples or other means may be arranged above the sample carrier.

With precise examination methods, especially using high-performance objectives with a numerical apparatus of more than 0.7, for example, are employed, however, examining the sample through a transparent bottom of a sample carrier is disadvantageous in that both the thickness and the refractive index of the sample carrier bottom affect the path of the rays. Due to such an influence, the size and/or the shape of the measuring volume present in a liquid sample, for example, may change. This causes corruption in the measurement results.

Especially in fluorescence spectroscopy, wherein, for example, the fluorescence of materials irradiated by a laser or another light source to obtain measurement results, even very small changes in the size and/or the shape of the measuring volume cause a deterioration of the measurement results. Tests have shown that when the thickness of the transparent bottom of the sample carrier changes by more than 5 μm and/or when the refractive index of the sample carrier bottom changes in the third position behind the point, the focus quality is already deteriorated such that a deterioration of the measurement results occurs.

To correct for the thickness of the sample carrier bottom, it is known to manually set the nominal thickness of the sample carrier bottom at an adjusting ring of the objective. To this avail, the corresponding adjusting ring of the objective is provided with a scaling where the thickness of the sample carrier bottom may be adjusted according to the indications by the manufacturer of the sample carrier. This is a rather troublesome process, since, in order to obtain acceptable measurement results, an operator of the device has to check for each sample carrier bottom whether the thickness indicated by the manufacturer has changed. It is another disadvantage of this procedure that inexact indications by the manufacturer are not detected and, thus, an unperceived corruption of the measurement results can occur. Especially, a manual adjustment using an adjusting ring at the objective is not suited to correct variations of the thickness within a sample carrier bottom. It is another disadvantage that the refractive index of the sample carrier bottom is not taken into account when adjusting the nominal thickness of the sample carrier bottom. A slight material variation in the sample carrier bottom which may already cause relevant changes in the refractive index, can thus not be accounted for by using the adjusting ring.

It is the object of the invention to provide a method for correcting for the size and/or the shape of a measuring volume in a chemical and/or a biological sample, wherein negative effects caused by a sample carrier bottom, especially caused by variations in the thickness and refractive index thereof, are corrected. It is another object of the invention to provide a device for performing the method.

SUMMARY OF THE INVENTION

According to the invention, the object is solved with the features of various embodiment. In particular, in accordance with one embodiment of the invention, a method for correcting the size and/or shape of a measuring volume, (18) in a chemical and/or biological sample (14), especially in fluorescence spectroscopy, is provided that includes the steps of: (a) imaging a measuring volume (18) locate within the sample (14) to a detector means (44), using observing optics (34), the imaging being effected through a sample carrier wall (16) of a sample carrier (12) containing the sample (14); (b) automatically determining the thickness of the sample carrier wall (16); and (c) automatically shifting at least one lens (28) along an optical axis of the observing optics (34) to correct the size and/or shape of the measuring volume (18) as a function of the thickness of the sample carrier wall (16). In accordance with another embodiment of the invention, a method for correcting the size and/or shape of a measuring volume (18) in a chemical and/or biological sample (14), especially in fluorescence spectroscopy, is provided that includes the steps of: (a) irradiating the sample (14) arranged in a sample carrier (12) with electromagnetic radiation to excite fluorescence of particles present in the sample (14); (b) imaging a measuring volume (18) located within the sample (14)10 a detector means (44), using observing optics (32), the imaging being effected through a sample carrier wall (16) of a sample carrier (12) containing the sample (14); (c) automatically shifting at least one lens (28) along the optical axis of the observing optics (32) to change the size and/or the shape of the measuring volume (18); (d) determining the radiation amount as a function of the position of the at least one lens (28) using the detector means (44) and/or a control means (42) coupled thereto; and (e) adjusting the position of the lens (28) at the maximum radiation amount to correct the thickness of the sample carrier wall (16). In accordance with yet another embodiment of the invention, a device for performing the above methods is provided that includes: (a) observing optics (32) for observing the measuring volume (18); (b) a detector device (44) for detecting the radiation emitted by the sample (14) or the reflections caused by the sample carrier wall (16); (c) an adjusting means (40) for automatically shifting at least one lens (38) along the optical axis of the observing optics (32); and (d) a control means (42) for controlling the adjusting means (40) depending on the radiation captured by the detector means (44).

In a first embodiment of the present method, a measuring volume located within a sample is imaged on a detector means using observing optics. Especially in fluorescence spectroscopy, employed, for example, in high-throughput screening, the measuring volumes preferably have a size of less than 20 fl, in particular less than 10 fl. In the next step of the present method, the thickness of the sample carrier wall, such as the sample carrier bottom through which the measuring is done, is assessed automatically. Determining the thickness of the sample carrier wall may be effected, for example, by ultrasound thickness measuring, eddie current thickness measuring, or capacitive thickness measuring. In the next step, at least one lens is automatically shifted along an optical axis of the observing optics. The degree of shifting depends on the previously determined thickness of the sample carrier wall. Thus, the size and/or the shape of the measuring volume are corrected depending on the optical thickness of the sample carrier wall.

Preferably, the degree in which the lens is shifted includes a shifting of the thickness of the sample carrier especially in view of its optical thickness, i.e. in consideration of the refractive index. Thus, it is particularly preferred to not only consider the physical thickness, but also the optical thickness of the sample carrier wall. To do so the optical thickness may be calculated from the physical thickness determined by the above method, for example, giving consideration to the refractive index. This is possible, for example, if the refractive index is known. Often, the refractive index is indicated by the manufacturer of the sample carrier wall used that may be of glass. Moreover, it is possible to determine the refractive index directly. This is advantageous in that deviations from the manufacturer's indications can also be considered. This may be done, for example, by determining the lateral deflection of a beam passed through the sample carrier bottom. For a more precise determination of the refractive index, the beam may be passed through the sample carrier bottom several times. This is advantageous, moreover, in that a detector for determining the lateral displacement of the beam can be provided on the same side of the sample carrier as an illumination means generating the beam.

The present invention for correcting for the size and/or the shape of a measuring volume is preferably executed on each sample carrier. Especially in screening, such as in high-throughput screening or medium-throughput screening, wherein titer plates with a plurality of samples, e.g., 1,536 or 2,080 samples, are measured, the method is run at least once, preferably several times per titer plate. Chips with channel structures or the like may also be used as sample carriers.

Preferably, the thickness of the sample carrier is determined by moving an illumination focus, i.e. a focal point of an optic means through the sample carrier wall. The movement may be effected by moving the sample carrier and/or by moving the illumination focus using an optic means. When moving the illumination focus through the sample carrier wall, reflections at the limiting surfaces of the sample carrier are detected. From the reflections occurring, the thickness of the sample carrier wall can be determined. This thickness takes into account the refractive index of the sample carrier wall so that a very good correction can already be achieved. However, the thickness of the sample carrier wall determined by the reflections occurring is not necessarily the optical thickness of the sample carrier wall. Generally, determining the optical thickness requires a further calculation giving consideration to the refractive index of the sample carrier wall. The refractive index is either known or may be determined as described above. Due to the measured thickness of the sample carrier wall, at least one lens is then automatically displaced along an optical axis of the observing optics so that the size and/or the shape of the measuring volume is corrected.

Determining the thickness of the sample carrier may be effected through separate observing optics. Preferably, however, the given optics of a microscope or another observing means is used. Especially in high-throughput screening methods, the illumination means, such as a laser, with which the sample to be examined is excited to fluorescence, may also be used to determine the thickness of the sample carrier bottom. To do so, for example, a beam splitter is provided in the beam path of the observing optics, through which beam splitter the light reflected by the sample carrier wall is decoupled from the measuring beam path and directed to a suitable detector. In particular, a pin diaphragm is arranged in front of the detector to allow an axial resolution of the reflected beams.

Preferably, the illumination focus is displaced through the sample carrier wall in increments or continuously.

Depending on the measurements performed, the measuring volume may be a relatively large volume. In particular, however, the measuring volume is the focus of the observing optics. Here, the focal point of the observing optics is arranged as the measuring volume within the sample. This is employed especially in high-throughput screening, since, due to a very small focus, it is possible to examine samples of a few μl within sample receiving portions (wells) of titer plates, without interfering reflections occurring at the inner walls of the wells.

Especially in fluorescence spectroscopy or other methods using the fluorescence of matter it is possible to use the electromagnetic radiation, which serves to excite fluorescent particles in the sample, also to determine the thickness of the sample carrier.

It is particularly preferred to consider the optical thickness of the sample carrier wall in correcting for the size and/or the shape of the measuring volume.

In a second preferred embodiment, the size and/or the shape of a measuring volume in a chemical and/or biological sample is not corrected by direct measurement of the thickness of the relevant sample carrier wall through which the measuring/examination of the sample is effected, but immediately by detecting the size of the measured volume. Here, the thickness of the sample carrier wall is simultaneously corrected regardless of the actual refractive index of the sample carrier wall. This method is suitable for examining very small sample volumes, especially in fluorescence spectroscopy and, particularly preferred, in screening, such as high-throughput screening and medium-throughput screening.

According to the invention, the samples arranged in a sample carrier, such as a well of a titer plate or a channel or the like of a chip, are irradiated with electromagnetic radiation for exciting fluorescence of particles in the sample. The particles may be fluorescent markers, color markers or material of the sample that fluoresce immediately, i.e. without providing a marker. Excitation with electromagnetic radiation causes emission of fluorescent radiation by the particles correspondingly excited. In the next step, using observing optics, the measuring volume located in the sample is imaged to a detector means, such as a CCD camera, preferably a detector with single photon resolution, such as PMT or APD detectors, for example. Here, the imaging is effected through a sample carrier wall, such as the sample carrier bottom, for example, which may be of glass or a transparent plastics material.

In the next step of this preferred embodiment, at least one lens is displaced automatically along the optical axis of the observing optics so that the size and/or the shape of the measuring volume is changed. By changing the size of the measuring volume, the amount of radiation detected by a detector means changes. This is based on the insight that the fluorescence of a particle, e.g. a molecule, is proportionate to the illumination intensity. The smaller the measuring volume, the higher the illumination density in the measuring volume. As a result, the radiation intensity of the individual particle or molecule increases.

Due to the variations in the radiation intensity of the particles/molecules in the sample, i.e. the amount of radiation, determined upon displacing the at least one lens of the observing optics, the lens may be automatically shifted to a position where maximum radiation intensity occurs. This causes a correction of the thickness of the sample carrier wall, since the measuring volume is minimal with a maximum radiation intensity of the particles/molecules. Here, the refractive index as well as the optical thickness of the sample carrier wall is considered automatically without any additional calculation. This embodiment of the present method especially also takes into account an emission media or the like present on the sample carrier wall.

The setting of the minimal measuring volume may be effected within predetermined limits, if a minimum size of the measuring volume is desired, for example. Preferably, the focus of the observing optics is located in the sample to be measured, so that the focus corresponds to the measuring volume and may be minimized using the present method.

When determining the radiation intensity, it may happen that despite a changing size of the measuring volume no significant change in the detected photons (radiation amount) occurs. This is the case, for example, when, due to the reduction of the measuring volume the number of molecules decreases, yet the same are excited stronger due to the increase in illumination intensity. Both effects can almost cancel each other out so that an exact determination of the optimum or the minimum size of the measuring volume is not possible. Therefore, preferably, the variation in intensity is determined in addition or instead of the radiation intensity. By determining the variation in intensity over time, the size of the measuring volume can be determined more exactly. In a relatively large measuring volume, for example, individual molecules or fluorescent particles entering and exiting cause no large variations since the large measuring volume contains a great number of fluorescent particles and the entering or exiting of single molecules causes only little change in the percentage of particles in the measuring volume. Accordingly, the variation in intensity are relatively small in large measuring volumes. In contrast, in small measuring volumes, the variations caused by an entering and/or exiting fluorescent particle are substantially greater. If, for example, a fourth particle enters a measuring volume containing only three fluorescent particles, the intensity increases by about ⅓. Preferably, the position of a measuring volume, i.e., preferably of the measuring focus, is adjusted when the variation in intensity is at its maximum, since the size of the measuring volume is minimal in this case. Preferably, the amplitude of the variation in intensity is determined.

Preferably, the size/shape of the measuring volume is calculated based on the following equation using a calculating means $$\frac{<I^2(t)> - <I(t)>^2}{<I(t)>^2}$$

wherein
$<I^2(t)>$: average value of the square function,
$<I(t)>^2$: square of the average value of the function,
I(t): course in time of the function, wherein
I=intensity of a function of time t, and
$< >$: forming an average value.

The invention further refers to a device for performing the present methods. To do so, the device comprises observing optics for observing the measuring volume which may be arranged in a well of a titer plate, for example. Further, a detector means for detecting the radiation emitted from the sample and/or the reflections caused by the sample carrier wall. Further, an adjusting means is provided for automatically displacing at least one lens along the optical axis of the observing optics. Thus, a change in the size of the measuring volume or a moving of a focus through the sample carrier wall can be effected. A control means is used to control the adjusting means and thus the position of at least one lens relative to the optical axis of the observing means, depending on the radiation captured by the detector means.

Preferably, the observing optics comprises an adjusting ring actuatable by the adjusting means for displacing the at least one lens. This may be, for example, the correction ring known from the manual setting of a correction value, which ring is automatically operated through a suitable adjusting means. This is advantageous in that existing observing optics can be retrofitted so that the present automatic methods can be performed after a retrofitting of existing examining means.

The following is a detailed description of preferred embodiment with respect to the accompanying drawings.

BRIEF DESCRIPTION OF THE DRAWINGS

In the Figures.

DETAILED DESCRIPTION OF THE INVENTION

Figure 1:
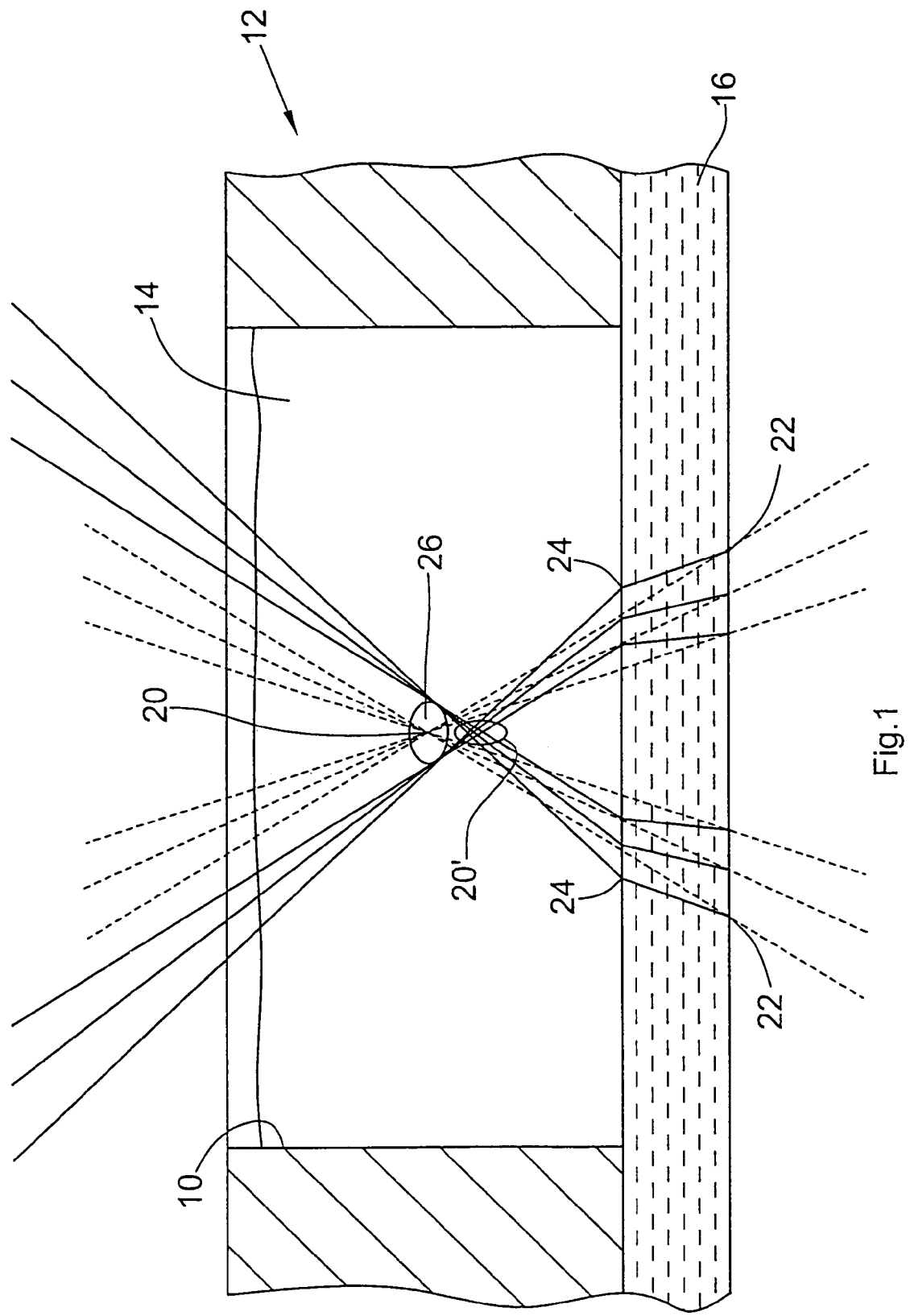
FIG. 1 is a schematic view of a measuring volume arranged in the sample volume.

In a well 10, i.e. a mostly cylindrical depression in a titer plate 12, a chemical and/or biological sample liquid 14 to be examined is located. The titer plate 12 is closed with a transparent sample carrier bottom 16, preferably of glass. If no visible light is used in examining the sample 14, the sample carrier bottom need not be transparent. It would then suffice that the sample carrier bottom 16 is permeable to the radiation employed.

A measuring volume generated in the sample 14 by an illumination means and through an optical means and having the shape of the focus 20 of the observing means ideally comprises an extremely small, almost point-shaped size. The focus or focal point 20 should be situated within the sample 14, the focus itself has a certain dimension that is varied by the refraction of the beam path occurring in a sample carrier bottom 16.

An unaffected beam path is illustrated in broken lines in FIG. 1. from this results the represented size of the measuring volume as the focus 20. At the interface, i.e. at the medium transition between air and glass, for example, i.e. at the point 22, the sample carrier bottom refracts the beams. When leaving the sample carrier bottom, the beams are again refracted at the points 24 due to the presence of two different media (e.g. glass and sample liquid). This results in an enlarged measuring volume represented by a solid line 26. The enlargement of the measuring volume is effected by a displacement and a distortion of the focus 20 into the area 20' as a result of the above described refractions. However, since observing optics view the focal point 20 or the corresponding horizontal surface in FIG. 1, respectively, the enlarged focus 26 is perceived.

Figure 2:
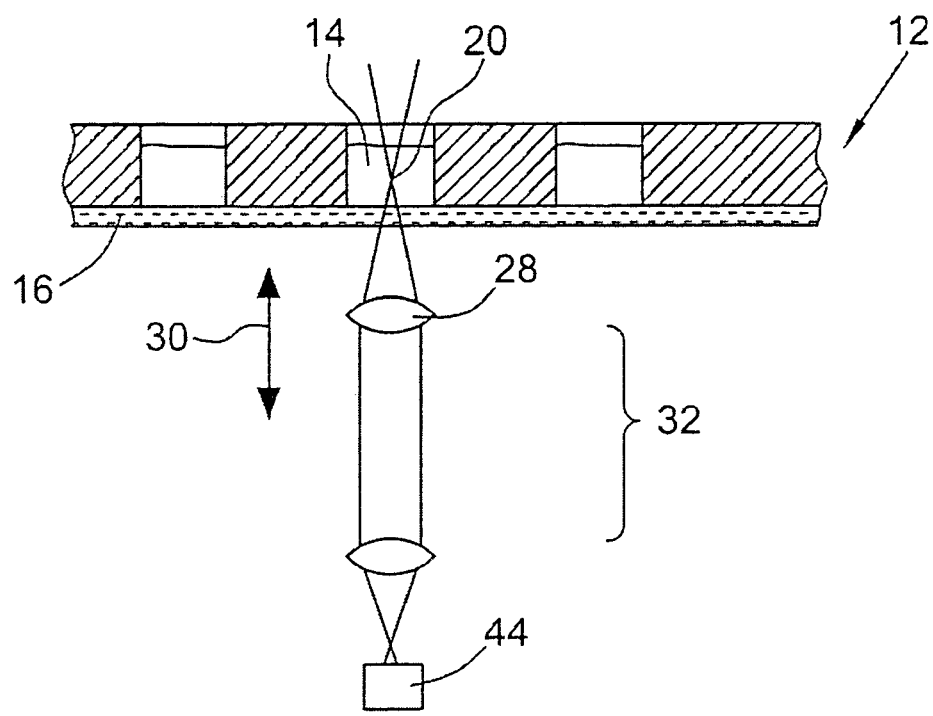
FIG. 2 illustrates a schematic principle structure of the present device.

By shifting a lens 28 (FIG. 2) along an arrow 30, i.e. along an optical axis of observing optics 32, the size of the focus 20 can be varied.

A preferred optimizing of the size of the measuring volume is effected by measuring the variation in intensity within the focus 20, preferably using a higher-level moment analysis.

Figure 3:
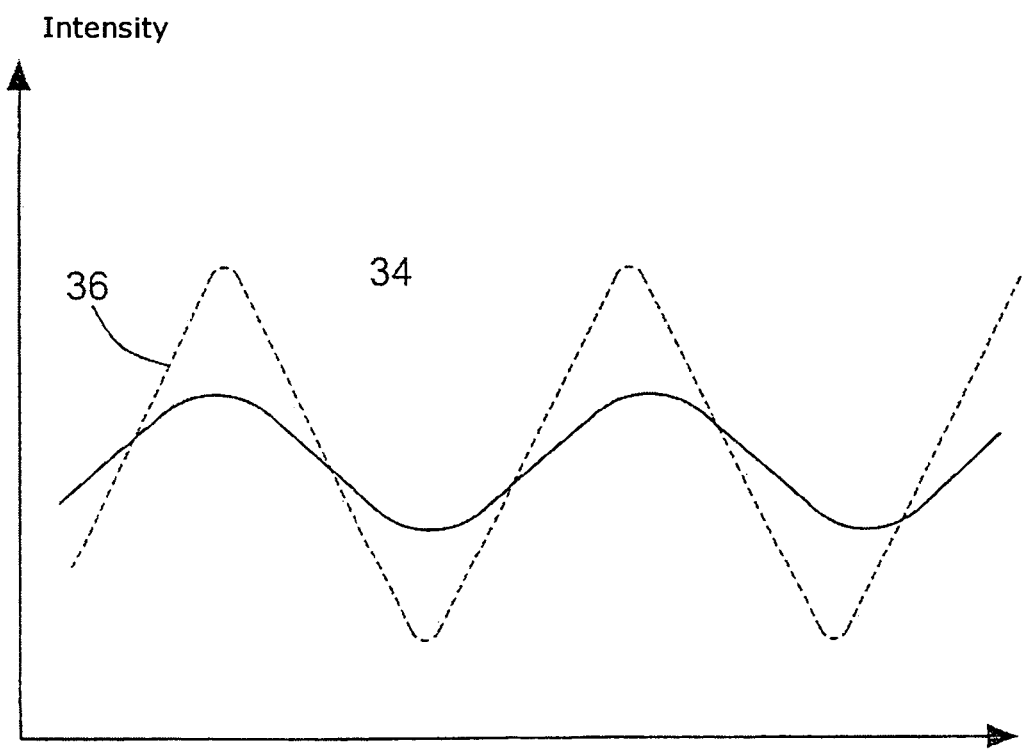
FIG. 3 is a schematic diagram of the intensity versus time.

FIG. 3 illustrates two curves 34, 36 showing the basic difference between a small and a large focus or measuring volume. With a rather large focus, a variation in intensity, as in curve 34, has a rather small amplitude. This is due to the fact that with a relatively large focus, in which 20 fluorescent particles exist, for example, a change in the particle number by one or two fluorescent particles has only little effect.

With a smaller focus, a variation in intensity occurs as basically illustrated by the broken line curve 36. In this case, the variation in intensity is substantially greater, since, with a small focus that includes only 3 fluorescent particles, for example, even a single particle entering or exiting this focus causes a substantial increase in fluorescence. Due to the present implementation of the higher-level moment analysis for examining the variations in intensity, the lens 28 (FIG. 2) can be shifted in a simple manner using a control unit, so as to set the size of a measuring volume 18, preferably the minimum size of the measuring volume 18.

Preferably, to shift the lens 28 located in an objective 38 (FIG. 4) that corresponds to the observing optics 32, an adjusting means 40 is used that is coupled to a control means 42. Via the control means 42, which is coupled to a detector 44 (FIG. 2), the necessary displacement of the lens 28 in the objective 38 is determined. The control means 42 controls the adjusting means which preferably comprises a transmission means 44 in the form of a screw drive. The screw drive engages an adjusting ring 46. The adjusting ring 46 may be the adjusting ring of a known objective, which ring may be knurled, for example, where the lens 28 may be displaced manually using the adjusting ring so as to compensate for the thickness of a sample carrier bottom 16. By turning the screw drive 44 that engages the adjusting ring 46, the adjusting ring 46 is rotated and thus the lens 28 arranged in the objective 38 is displaced. Hereby, as described above, the size of the focus 20 is varied.

Figure 4:
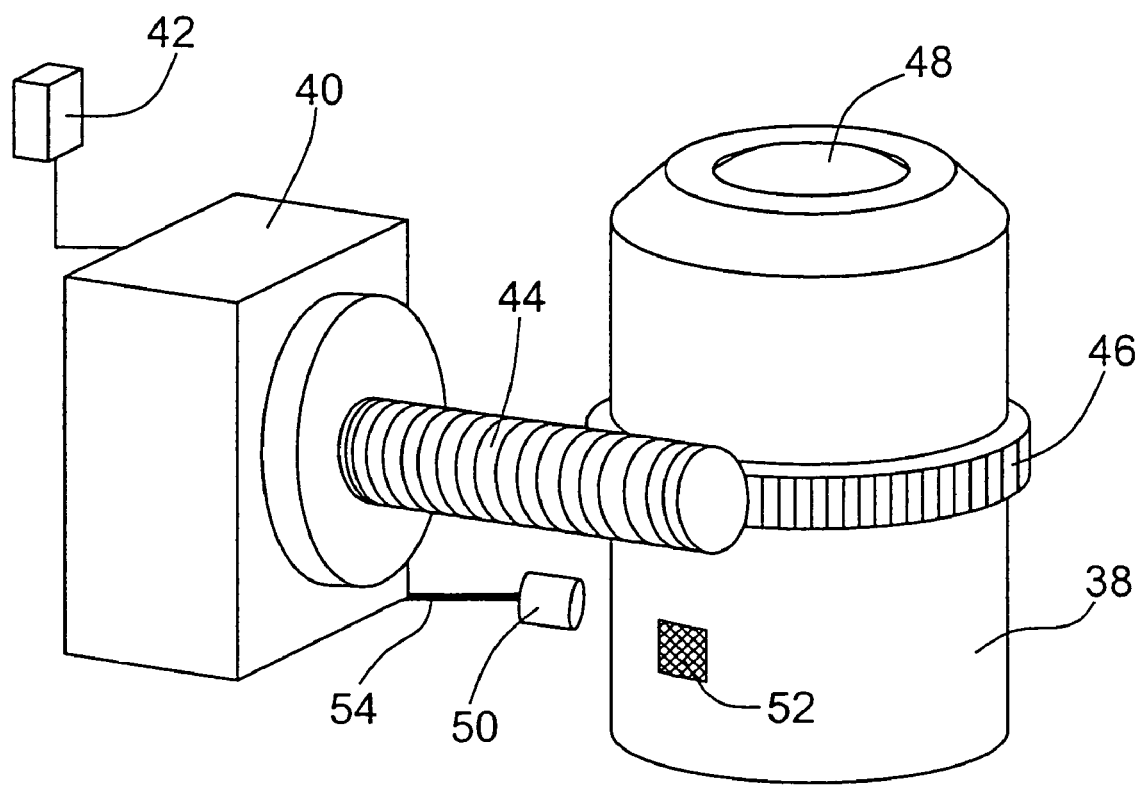
FIG. 4 is a schematic perspective view of a preferred embodiment of the device.

The device illustrated in FIG. 4 can thus be employed in the present method, wherein the thickness of the sample carrier bottom 16 is determined independent of the radiation emitted by a sample, as well as in the present method, wherein the size of the focus 20 is adjusted by means of the radiation intensity and/or the variation in intensity.

If the objective 38 is an objective wherein turning the adjusting ring 46 causes a movement of an exit lens 48, a stop switch 50 is preferably provided to avoid damage to the objective mechanics. The stop switch may be a suitable sensor, for example, which emits light beams towards the objective 38. As soon as a reflective reference surface 52 attached to the objective 38 enters the area of the sensor 50, the sensor 50 generates a signal that is transmitted to the adjusting means 40 via a line 54. The signal causes the screw drive 44 to stop.

The invention claimed is:

1. Method for correcting for the size and/or shape of a measuring volume in a chemical and/or biological sample, especially in fluorescence spectroscopy, comprising the steps of:
    imaging a measuring volume located within the sample to a detector means, using observing optics, the imaging being effected through a sample carrier wall of a sample carrier containing the sample,
    automatically determining the thickness of the sample carrier wall, and
    automatically shifting at least one lens along an optical axis of the observing optics to correct for the size and/or shape of the measuring volume as a function of the thickness of the sample carrier wall.

2. Method of claim 1, wherein the optical thickness is determined.

3. Method of claim 1, wherein the thickness of the sample carrier wall is determined by:
    moving an illumination focus through the sample carrier wall using an optical means, and
    detecting the reflections occurring at the interfaces of the sample carrier when moving the illumination focus.

4. Method of claim 3, wherein the illumination focus is moved by means of the observing optics.

5. Method of claim 3, wherein the illumination focus is moved incrementally or continuously through the sample carrier wall.

6. Method of claim 5, wherein the focus of the observation optics defines the measuring volume.

7. Method of claim 1, wherein the lens is displaced using a high-precision electric drive.

8. Method of claim 1, wherein the sample is irradiated with electromagnetic radiation to excite fluorescence in particles present in the sample.

9. Method of claim 8, wherein the electromagnetic radiation is used to determine the thickness and/or the optical thickness of the sample carrier wall.

10. Method of claim 1, wherein, especially in a screening process such as in high-throughput screening or medium-throughput screening, the thickness of the sample carrier wall of each sample carrier is determined at least once.

11. Method for correcting the size and/or shape of a measuring volume in a chemical and/or biological sample, especially in fluorescence spectroscopy, comprising the steps of:
    irradiating the sample arranged in a sample carrier with electromagnetic radiation to excite fluorescence of particles present in the sample,
    imaging a measuring volume located within the sample to a detector means, using observing optics, the imaging being effected through a sample carrier wall of a sample carrier containing the sample,
    automatically shifting at least one lens along the optical axis of the observing optics to change the size and/or the shape of the measuring volume,
    determining the radiation amount as a function of the position of the at least one lens using the detector means and/or a control means coupled thereto, and
    adjusting the position of the lens at the maximum radiation amount to correct for the thickness of the sample carrier wall.

12. Method of claim 11, wherein the variation in intensity is determined in addition or instead of the radiation intensity.

13. Method of claim 12, wherein the position of the lens is set when the variation in intensity is at its maximum.

14. Method of claim 11, wherein the amplitude of the variation in intensity is determined in addition or instead of the radiation intensity.

15. Method of claim 14, wherein the position of the lens is set when the amplitude is at its maximum.

16. Method of claim 14, wherein the position of the lens is calculated based on the equation $$\frac{<I^2(t)> - <I(t)>^2}{<I(t)>^2}.$$

17. Method of claim 11, wherein, especially in a screening process, the thickness of the sample carrier wall of each sample carrier is determined at least once.

18. Device for performing a method for correcting for the size and/or shape of a measuring volume in a chemical and/or biological sample, especially in fluorescence spectroscopy, the device comprising:
   observing optics for observing the measuring volume,
   a detector means for detecting the radiation emitted by the sample or the reflections caused by the sample carrier wall,
   an adjusting means for automatically shifting at least one lens along the optical axis of the observing optics, wherein the adjusting means automatically shifts at least one lens along the optical axis of the observing optics to correct for size and/or share of the measuring volume as a function of thickness of the sample carrier wall, and
   a control means for controlling the adjusting means depending on the radiation captured by the detector means.

19. Device of claim 18, wherein the observing optics has an adjusting ring for displacing the lens, the ring being actuatable by the adjusting means.

20. Device of claim 19, wherein the adjusting means comprises a transmission means, especially a screw drive engaging a toothing of the adjusting ring, the transmission means being coupled to the adjusting means.

21. Device of claim 19, wherein a stop switch is coupled to the adjusting ring, or the transmission means, or the adjusting ring and the transmission means.

22. Method of claim 11, wherein, especially in a screening process, the thickness of the sample carrier wall of each sample carrier is determined at least three times.

23. Method of claim 11, wherein, especially in a screening process, the thickness of the sample carrier wall of each sample carrier is determined at least five times.

24. Method of claim 1, wherein, especially in a screening process such as in high-throughput screening or medium-throughput screening, the thickness of the sample carrier wall of each sample carrier is determined at least three times.

25. Method of claim 1, wherein, especially in a screening process such as in high-throughput screening or medium-throughput screening, the thickness of the sample carrier wall of each sample carrier is determined at least five times.

* * * * *